US007921468B2

(12) United States Patent
Sutton

(10) Patent No.: US 7,921,468 B2
(45) Date of Patent: Apr. 12, 2011

(54) EYE AND EAR PROTECTOR

(76) Inventor: Daniel Joseph Conrad Sutton, Cottageville, SC (US)

(*) Notice: Subject to any disclaimer, the term of this patent is extended or adjusted under 35 U.S.C. 154(b) by 178 days.

(21) Appl. No.: 12/354,332

(22) Filed: Jan. 15, 2009

(65) Prior Publication Data
US 2010/0175173 A1 Jul. 15, 2010

(51) Int. Cl.
*A61F 9/02* (2006.01)
*A61F 9/04* (2006.01)
*A41D 13/11* (2006.01)
*A61F 9/00* (2006.01)

(52) U.S. Cl. ............ 2/9; 2/11; 2/12; 2/13; 2/15
(58) Field of Classification Search .............. 2/455, 410, 2/423, 424, 15, 11, 12, 13, 426–431, 439–448, 2/453, 454, 9
See application file for complete search history.

(56) References Cited

U.S. PATENT DOCUMENTS

| | | | | |
|---|---|---|---|---|
| 3,297,832 A * | 1/1967 | Brown | | 381/327 |
| 3,431,370 A * | 3/1969 | Crosby | | 181/131 |
| 3,667,834 A * | 6/1972 | Davison et al. | | 351/118 |
| 3,671,111 A * | 6/1972 | Okner | | 351/113 |
| 3,856,007 A * | 12/1974 | Leight | | 128/866 |
| 3,943,925 A * | 3/1976 | Leight | | 128/866 |
| 4,153,348 A * | 5/1979 | Walters et al. | | 351/118 |
| D262,491 S * | 12/1981 | Ebert | | D24/106 |
| 4,810,080 A * | 3/1989 | Grendol et al. | | 351/41 |
| 4,902,120 A * | 2/1990 | Weyer | | 351/158 |
| 4,932,771 A * | 6/1990 | Nowottny | | 351/113 |
| 4,955,708 A * | 9/1990 | Kahaney | | 351/44 |
| D318,283 S * | 7/1991 | Cleveland | | D16/330 |
| 5,133,596 A * | 7/1992 | Korny et al. | | 351/158 |
| 5,170,502 A * | 12/1992 | Hegendorfer et al. | | 2/13 |
| 5,257,050 A * | 10/1993 | Wiedner | | 351/86 |
| 5,357,292 A * | 10/1994 | Wiedner | | 351/105 |
| 5,381,192 A * | 1/1995 | Canavan et al. | | 351/118 |
| 5,475,449 A * | 12/1995 | Pyle | | 351/123 |
| 5,532,767 A * | 7/1996 | Pleune et al. | | 351/118 |
| 5,606,743 A * | 2/1997 | Vogt et al. | | 455/347 |
| 5,703,670 A * | 12/1997 | Callard | | 351/123 |
| 5,781,272 A * | 7/1998 | Bright et al. | | 351/123 |
| 5,959,715 A * | 9/1999 | Jaffelin | | 351/113 |
| D426,845 S * | 6/2000 | Green et al. | | D16/309 |
| 6,138,790 A * | 10/2000 | Leight | | 181/130 |
| D435,058 S * | 12/2000 | Green et al. | | D16/309 |
| 6,176,576 B1 * | 1/2001 | Green et al. | | 351/123 |
| 6,382,213 B1 * | 5/2002 | Sanpei | | 128/864 |
| 6,604,823 B2 * | 8/2003 | Hursey, Jr. | | 351/61 |
| 6,728,974 B2 * | 5/2004 | Wadsworth | | 2/456 |
| 6,843,562 B1 * | 1/2005 | Ng | | 351/118 |
| 6,950,531 B2 * | 9/2005 | Rickards | | 381/381 |
| 7,020,903 B2 * | 4/2006 | Artzberger | | 2/431 |
| 7,133,532 B2 * | 11/2006 | Rickards | | 381/327 |
| 7,213,916 B1 * | 5/2007 | Pettett | | 351/158 |
| D558,815 S * | 1/2008 | Laborte | | D16/309 |
| D561,233 S * | 2/2008 | McLaughlin | | D16/315 |

(Continued)

Primary Examiner — Bobby H Muromoto, Jr.
(74) Attorney, Agent, or Firm — B. Craig Killough

(57) ABSTRACT

Protective eyeglasses provide hearing protection from elevated noise levels. The protective eyeglasses have safety lenses for protection of each of the eyes. Support members extend from the lenses of the eyeglasses to the ears, and have earplugs or protectors thereon which are inserted into the ears. The side support members are spring biased towards each other so that the side members provide pressure to hold the plugs in the ears of the wearer. Ear plugs are mounted so as to swivel relative to the side support members. The side support members are telescoping and are adjustable in length.

12 Claims, 4 Drawing Sheets

U.S. PATENT DOCUMENTS

| | | | |
|---|---|---|---|
| 7,641,334 B1* | 1/2010 | Goldie | 351/123 |
| 7,735,996 B2* | 6/2010 | van der Zwan et al. | 351/158 |
| 2002/0024630 A1* | 2/2002 | Hornig | 351/41 |
| 2002/0067461 A1* | 6/2002 | Bell | 351/128 |
| 2004/0141147 A1* | 7/2004 | Cyr | 351/41 |
| 2005/0206837 A1* | 9/2005 | Toulch | 351/110 |
| 2005/0270475 A1* | 12/2005 | Curci et al. | 351/69 |
| 2007/0253588 A1* | 11/2007 | Sanpei | 381/381 |
| 2007/0263168 A1* | 11/2007 | Cohen et al. | 351/135 |
| 2008/0169998 A1* | 7/2008 | Jacobsen et al. | 345/8 |

\* cited by examiner

EYE AND EAR PROTECTOR

FIELD OF THE INVENTION

This invention relates to safety devices generally, and is more specifically directed to a device for protecting eyes and ears of a user of the invention.

BACKGROUND OF THE INVENTION

It is frequently desirable to wear eye protection and ear protection. In many industrial and construction settings safety regulations make wearing safety glasses mandatory, and frequently, it is also mandatory to wear earplugs.

Accordingly, workers may be required to possess safety glasses, a left earplug and a right earplug. A worker may lose one or both earplugs, and not bother to wear earplugs. This omission may not be noticed by a supervisor. The failure to wear safety glasses and/or ear protection devices may result in a worker's loss of sight and/or hearing.

Employers may be subjected to substantial workers' compensation claims from the loss of sight or hearing. Since hearing loss may not be revealed for several years after periods of noise exposure, an employer may be subject to workers' compensation claims for events that occurred many years earlier.

There is a need for a device that will protect the eyes of a wearer from debris, projectiles, and similar hazards from foreign materials. Further, there is a need for eye protection that incorporates ear protection. The ear protection should not simply be present in the ears, but the ear protection must be sufficiently pressed into the ears to seal the ear from noise. At the same time, the safety device must be adaptable to a wide range of wearers, each of whom may have different distances from the bridge of the nose to the ears, with these distances varying three-dimensionally. A single device that protects the ears and eyes should be suitable for wear by a large percentage of the adult population.

SUMMARY OF THE INVENTION

The present invention is protective eyeglasses which also provide hearing protection from elevated noise levels. The protective eyeglasses have safety lenses for protection of each of the eyes. Support members extend from the lenses of the eyeglasses to the ears, and have earplugs or protectors thereon which are inserted into the ears. The side support members are spring biased towards each other so that the side members provide pressure to hold the plugs in the ears of the wearer. Ear plugs are mounted to swivel relative to the side support members. The side support members are telescoping and are adjustable in length.

DETAILED DESCRIPTION OF PREFERRED EMBODIMENTS

Figure 1:
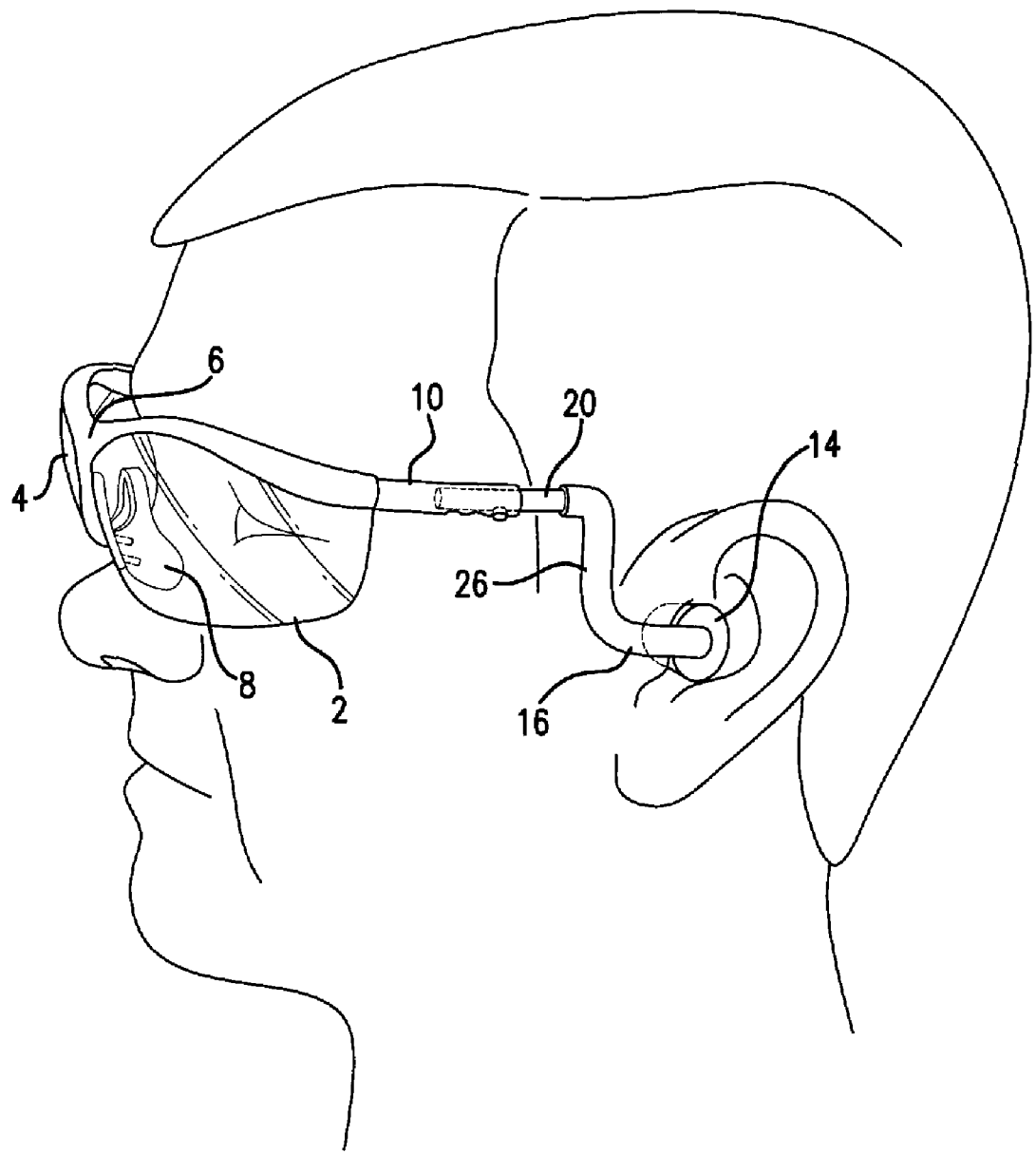
FIG. 1 is a view of a wearer wearing the safety device of the present invention.

FIG. 1 shows a typical wearer wearing the safety device of the present invention. In the embodiment as shown in FIG. 1, the device comprises eyeglasses having a left eye lens 2 and a right eye lens 4 connected by a bridge 6. A support member 8 fits over the bridge of the nose. A first side support member 10 extends from the left eye lens as shown in FIG. 1. A second side support member 12 extends from the right lens and along the side of the wearer's head. The side support members in one embodiment extend in a generally horizontal manner along each side of the wearer's head, and then extend downwardly and generally vertically, and then again extend generally horizontally into the ear of the wearer.

Each of the left eye lens and right eye lens are made of appropriate impact resistant materials that will resist the impact of debris or projectiles and are made to standards that are required and/or are common for safety glasses. The lenses may be formed of safety glass, or may be formed of impact resistant plastic or other impact resistant materials that are commonly used for safety glasses. The lenses may be transparent, or may be tinted as desired, or required, by the particular application.

Figure 3:
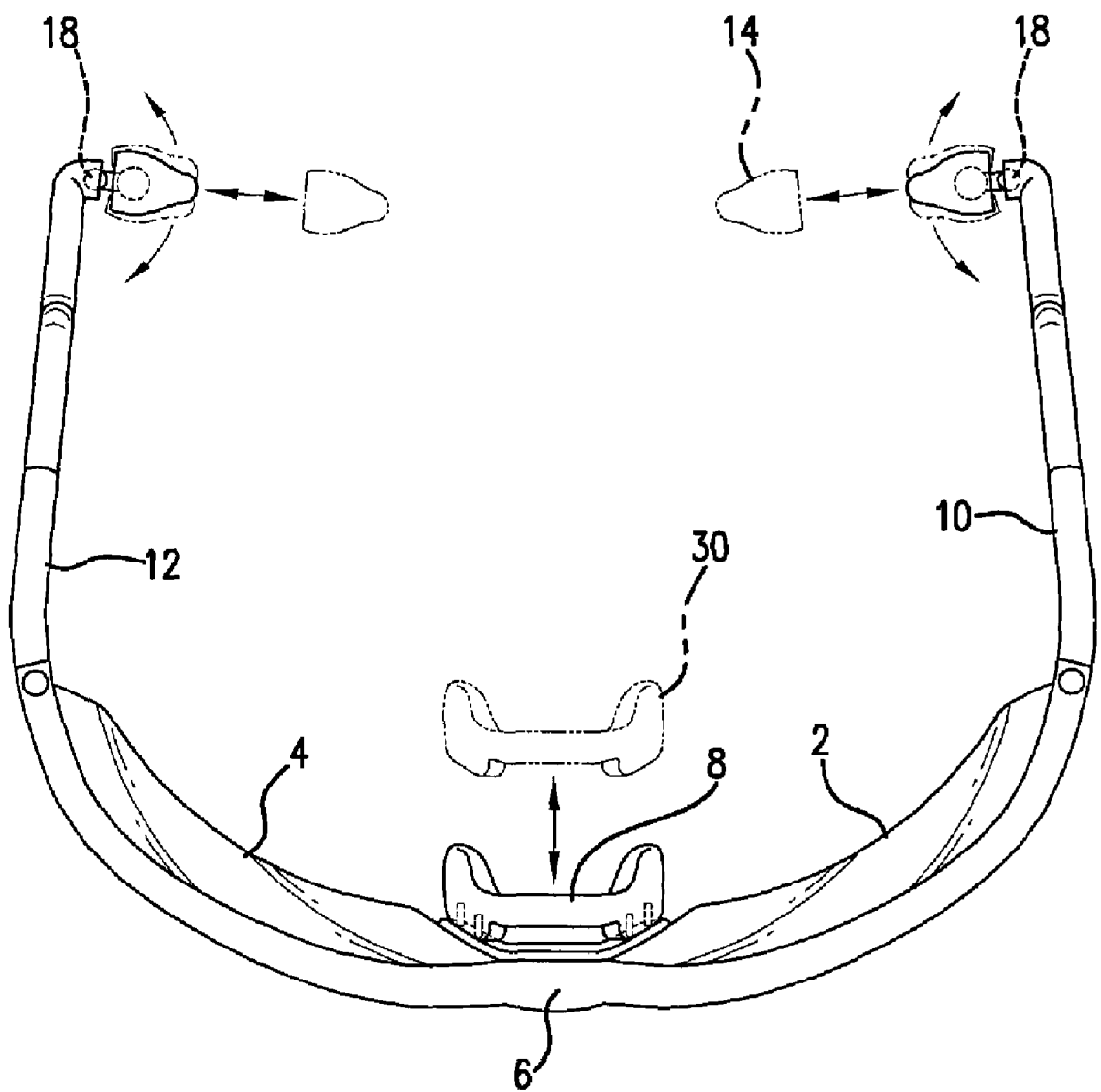
FIG. 3 is a top plain view of the safety device of the present invention demonstrating the ability of the earplugs to swivel relative to the support members, and further demonstrating that the pads which form the earplugs are removable, and that a pad which fits over the bridge of the nose to support the safety device is also removable.

As demonstrated by FIG. 3, the safety device of the present invention has a pad or earplug 14 that is mounted at or near the end of each of the side support members. The pad or plug is formed of a resilient material that is both comfortable to the wearer when the pads or plugs are inserted into the ear, and further, the resilient nature of the plug helps to seal the ear canal and helps to absorb sound which would enter the ear canal. The plugs are formed of generally tapered, or otherwise have a reduced dimension, on the end that is inserted into the ear, with a relatively larger dimension where the plugs attach to the side support members.

As demonstrated in FIG. 3, the plugs are mounted to the lower generally horizontal portion 16 of the side support members by a structure that allows the plugs to swivel, pivot and/or rotate. In the embodiment shown in FIG. 3, a ball and socket 18 relationship between the mounting point for the earplug and the side support member allows the earplugs to rotate relative to the side support members. This structure is one (1) feature which allows the device to be worn by a large number of users, irrespective of the dimensional relationships of the wearer's respective heads, eyes, ears and ear canals.

Figure 4:
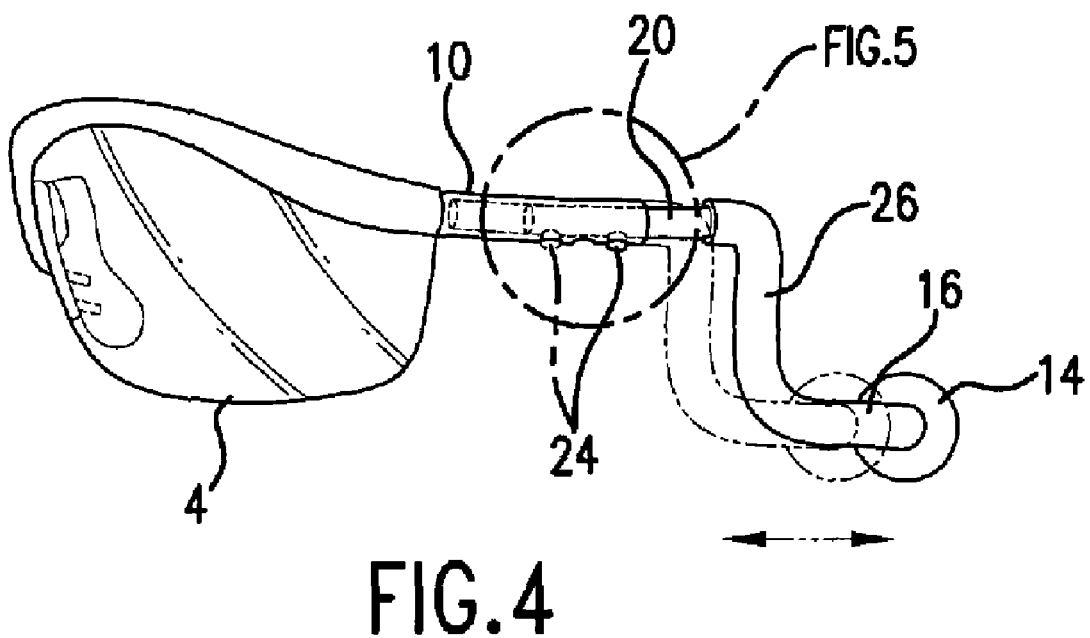
FIG. 4 is a left side elevation of the safety device demonstrating the telescoping feature of the left side support member.
Figure 5:
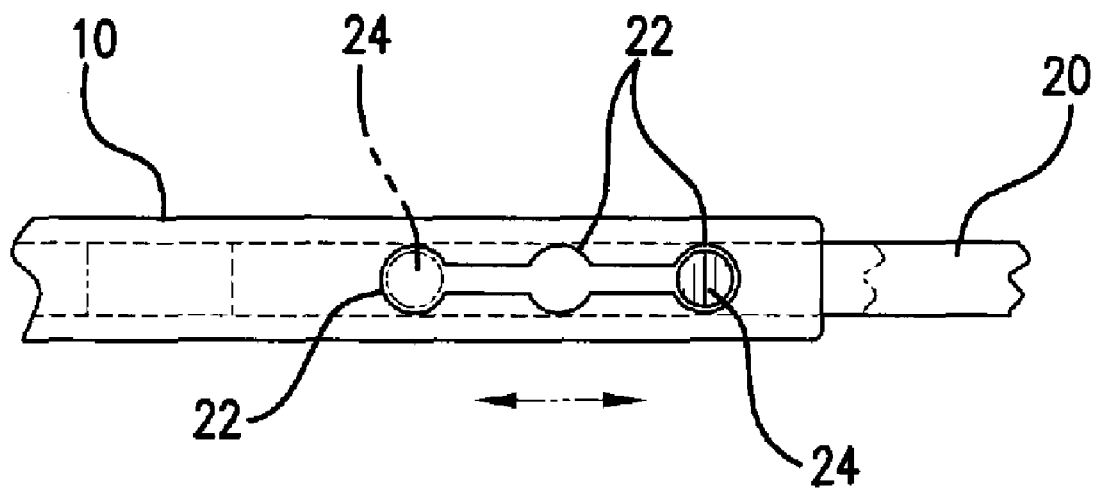
FIG. 5 is a sectioned view taken essentially as shown in FIG. 4, and demonstrating an embodiment of the telescoping member.

As demonstrated in FIG. 4, the side support members each telescope relative to the lens. This telescoping feature allows the relative length of the side support members to be extended or retracted, so that the distance of the earplugs to the bridge between the lenses can be lengthened or shortened. This is another feature which allows the glasses to be worn by a relatively large percentage of the adult population.

In one embodiment, the telescoping feature comprises a slidable member 20 that engages the side support 10 locks by a series of detents 22 and a pin 24 that engages the detents. The pin may be spring biased and mounted to the slidable member 20. The pin may be pressed inwardly to remove it from the relatively large opening provided by the detents, and moved to another detent having a relatively large opening. As shown, there are three (3) detents in each side support member. Other known methods and devices for telescoping may be used.

In another embodiment, the member 26 that adjoins the side support member and extends generally vertically downward from the side support members may be rotated relative to the side support member. This further allows adjustment of the device for more universal use by the population. It is important that, if this generally vertical member 26 rotates relative to the slidable portion 20 of horizontal side support member, that it be capable of locking or fixing in place, so that an inward pressure of the side support members pushing the earplugs into the ears of the user can be maintained.

It is important that the earplugs are retained within the ears. The fit of the earplugs within the ear should be such that that the earplugs contact the outer portion of the ear canal, and compress slightly. However, the earplugs should not be uncomfortable to the wearer, or present a risk of injury to the wearer.

Figure 2:
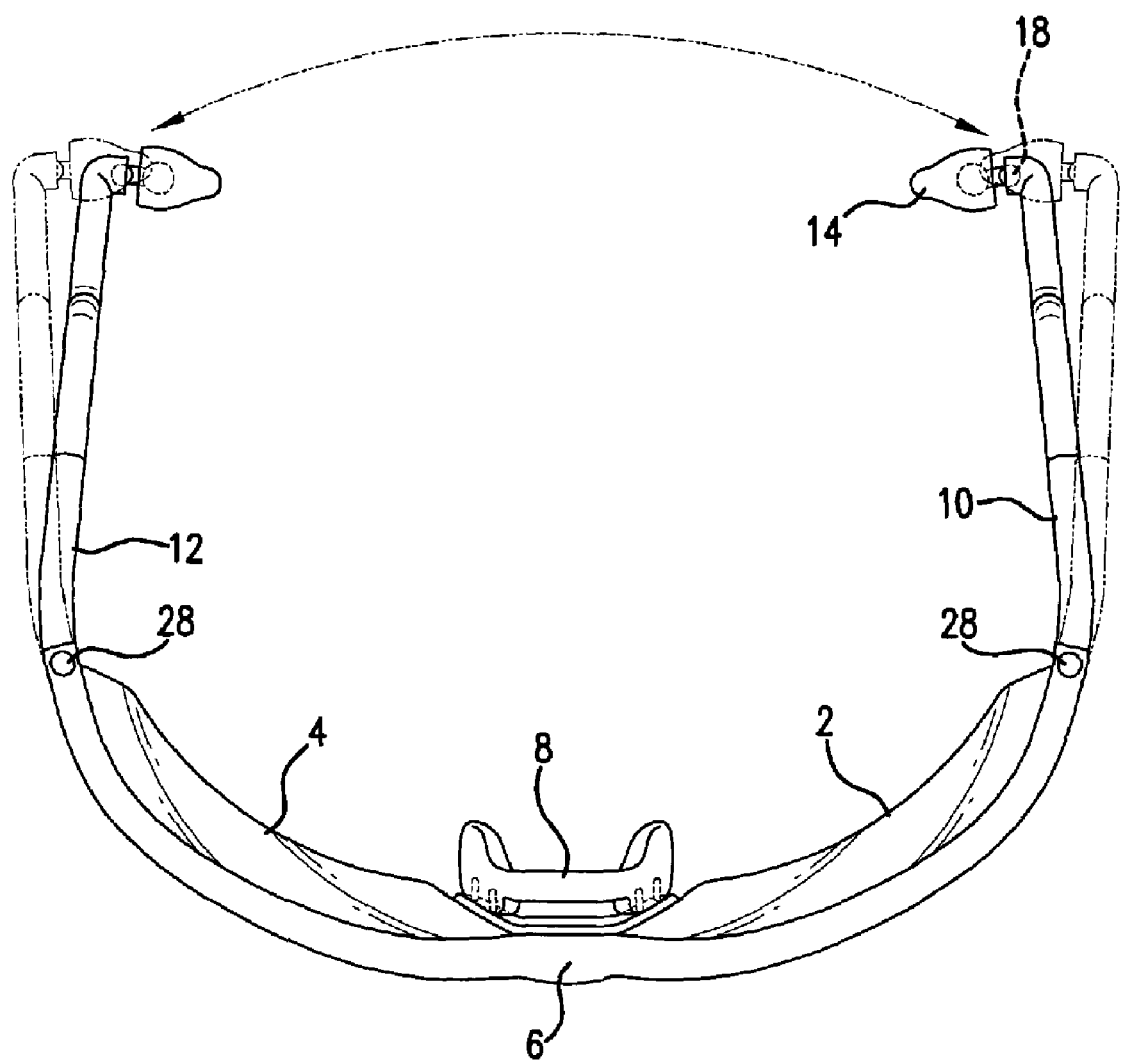
FIG. 2 is a top plan view of the safety device of the present invention, demonstrating spring biasing of the side members.

As shown in FIG. 2, the side support members 10,12 provide inward pressure on the earplugs. It is preferred that the side members are in a spring biased relationship with each other, such that each of the side members provides inward pressure, as demonstrated in FIG. 2. The dark lines of FIG. 2 demonstrate the position of the side support members in their normal state, with the phantom lines demonstrating the side support members being pushed outwardly as they are placed on the user's head and the earplugs are placed within the out ear canal of the wear. Spring biasing will urge the side support members toward the head of the user and push and hold the ear pads into the ear canals of the user.

Spring biasing pressure may be provided by the frame of the eyeglasses, such as at the bridge 6 of the eyeglasses, due to the materials used. Many plastic materials will provide sufficient inward pressure as required by the invention, so that the side support members may move relative to each other as demonstrated by FIG. 2. Alternatively, spring biasing may be provided in the optional hinge 28 where the side support members join the lenses, or spring biasing may be provided in the frame that supports the lenses of the eyeglasses.

The bridge of the eyeglasses should also be comfortable for the wearer, and accommodate wearers in a substantially universal manner, so that a large percentage of workers can wear the device. The removable nose pad 30 may also assist in meeting this goal of the invention. The bridge 6 of the eyeglass frame is provided with a pad support, having a relatively wide opening. Removable pads of various sizes may be used to size the eyeglasses for comfort for the wearer, and also to better retain the glasses on the wearer. By using a pad that compresses, a large number of wearers can use the glasses, while at the same time, a compressible material such closed cell foam will help retain the glasses in place on the wearer's head.

What is claimed is:

1. Protective eyeglasses, comprising:
   a first lens having a first generally telescoping support extending therefrom wherein the first generally telescoping support comprises a first side support and a first slidable member that engages said first side support;
   a second lens having a second telescoping support extending therefrom, wherein the second telescoping support comprises a second side support and a second slidable member that engages said second side support;
   wherein the first slidable member comprises a first resilient plug member mounted thereto and the second slidable member comprises a second resilient plug member mounted thereto, and wherein the first plug member is mounted to the first slidable member in a relationship so that the first resilient plug member is mounted to pivot and swivel in three (3) dimensions relative to the first slidable member, and wherein the second plug member is mounted to the second slidable member in a relationship so that the second resilient plug member is mounted to pivot and swivel in three (3) dimensions relative to the second slidable member,
   wherein said first telescoping support member and second telescoping support member are in a spring biased relationship relative to each other, and said spring biased relationship urges said resilient plug members toward each other.

2. Protective eyeglasses as described in claim 1, wherein the first slidable member is constructed and arranged to be capable of rotation axially relative to the first side support, and wherein the second slidable member is constructed and arranged to be capable of rotation axially relative to the second side support.

3. Protective eyeglasses as described in claim 1, wherein the first plug member is mounted to the first slidable member by a ball and socket relationship so that the first resilient plug member is mounted to pivot and swivel in three (3) dimensions relative to the first slidable member, and wherein the second plug member is mounted by a ball and socket relationship to the second slidable member so that the second resilient plug member is mounted to pivot and swivel in three (3) dimensions relative to the second slidable member.

4. Protective eyeglasses as described in claim 1, wherein the first telescoping support member and the second telescoping support member are in a spring biased relationship relative to each other by spring biasing provided in a hinge that is present at an end of the first telescoping support member that is opposite the first resilient plug and by spring biasing provided in a hinge that is present at an end of the second telescoping support member that is opposite the second resilient plug.

5. Protective eyeglasses as described in claim 1, wherein the first slidable member and the second slidable member each comprise a generally horizontal member that slidably engages one of said first side support and said second side support, and wherein the first slidable member and the second slidable member each comprise a generally vertical member that extends downwardly from the associated generally horizontal member, and wherein the first slidable member and the second slidable member each comprise a second generally horizontal member that extends from the associated generally vertical member.

6. Protective eyeglasses as described in claim 1, wherein said first lens and said second lens are formed of plastic.

7. Protective eyeglasses as described in claim 1, wherein said first lens and said second lens are formed of shatter resistant safety glass.

8. Protective eyeglasses as described in claim 1, wherein the first telescoping support member and the second telescoping support member each comprise a locking device.

9. Protective eyeglass as described in claim 1, wherein the first telescoping support member and the second telescoping support member each comprise a locking device, and wherein said locking device comprises a detent.

10. Protective eyeglasses as described in claim 1, wherein a bridge of said eye glasses connects a first lens to a second lens, and wherein said bridge comprises a nose receiving area, and wherein said nose receiving area is constructed and arranged to receive removable pads, and wherein a size of said nose receiving area is selectively varied by application of removable pads of varying sizes.

11. Protective eyeglasses as described in claim 2, wherein the first slidable member and the second slidable member each comprise a generally horizontal member that slidably engages one of said first side support and said second side support, and wherein the generally horizontal member of the first slidable member rotates relative to the first side support and wherein the generally horizontal member of the second slidable member rotates relative to the second side support.

12. Protective eyeglasses as described in claim 2, wherein the first slidable member and the second slidable member each comprise a generally horizontal member that slidably engages one of said first side support and said second side support, and wherein the first slidable member and the second slidable member each comprise a generally vertical member that extends downwardly from the generally horizontal member, and wherein the first slidable member and the second slidable member each comprise a second generally horizontal member that extends from the associated generally vertical member, and wherein the generally horizontal member of the first slidable member rotates relative to the first side support and wherein the generally horizontal member of the second slidable member rotates relative to the second side support.

* * * * *